United States Patent [19]

Cavazza

[11] Patent Number: 5,180,850

[45] Date of Patent: Jan. 19, 1993

[54] CRYSTALLINE MAGNESIUM VALPORATE AND A METHOD FOR THE PREPARATION THEREOF

[75] Inventor: Claudio Cavazza, Roma, Italy

[73] Assignee: Sigma-Tau Industrie Farmaceutiche Riunite S.p.A., Rome, Italy

[21] Appl. No.: 626,910

[22] Filed: Dec. 13, 1990

[30] Foreign Application Priority Data

Dec. 22, 1989 [IT] Italy ............................... 22837 A/89

[51] Int. Cl.$^5$ ...................... C07B 53/00; A01N 37/00; A61K 31/19
[52] U.S. Cl. .................................................... 562/606
[58] Field of Search ......................... 562/606; 514/557

[56] References Cited

U.S. PATENT DOCUMENTS 4,895,873  1/1990  Schafer ............................... 562/606

FOREIGN PATENT DOCUMENTS 215530  11/1984  Fed. Rep. of Germany ...... 562/606
215533  11/1984  Fed. Rep. of Germany ...... 562/606

Primary Examiner—José G. Dees
Assistant Examiner—Joseph M. Conrad, III
Attorney, Agent, or Firm—Walter H. Schneider

[57] ABSTRACT

A new crystalline form of magnesium valproate obtained by reacting valproic acid with magnesium alkoxides in alcoholic solution is described.

The new crystalline form is endowed with enhanced bioavailability and may be used in a particularly pure form to prepare pharmaceutical compositions which are useful for treating Central Nervous System pathologies.

3 Claims, No Drawings

CRYSTALLINE MAGNESIUM VALPORATE AND A METHOD FOR THE PREPARATION THEREOF

DISCLOSURE

The present invention relates to a new crystalline form of magnesium di-n-propylacetate, as well as to a preparation method thereof and to pharmaceutical compositions containing said crystalline form thereof.

For a long time, di-n-propylacetic acid, usually known under the name of valproic acid, and the magnesium salt thereof, are known as therapeutic agents acting on the Central Nervous System, in particular as antiepileptic-anticonvulsivant agents, due to their capacity to modulate the cerebral amines and γ-aminobutyric acid (GABA).

Particularly, magnesium valproate drew researchers' attention by virtue of its improved pharmacological and pharmacokinetic distinctive features, especially as far as bioavailability is concerned. ES Patent 430062 discloses one method for the preparation of magnesium valproate including the reaction of valproic acid with magnesium oxide in alcholic medium.

The known method suffers from a set of drawbacks which adversely affects its use especially for the preparation of a therapeutic agent suited to pharmaceutical use.

As a matter of fact, since the reaction is carried out in a suspension (which requires a strong stirring and long reaction times), it leads to a final product contaminated with non reacted oxide that precipitates together with the product, when acetone is added to precipitate the magnesium salt.

According to the above method, moreover, the product is obtained essentially in an amorphous form, which is difficult to purify and dry and which has a poor bioavailability.

Finally, magnesium oxide is used in strong excess thus increasing the contamination of the final product.

According to the method of the invention, valproic acid is reacted with substantially stoichiometric amounts of magnesium alkoxides in alcoholic solution. Hence, the magnesium salt of valproic acid can be recovered with conventional methods, for instance by solvent evaporation, or adding acetone or other liquids in which magnesium valproate is insoluble.

The method of the invention, besides allowing the achievement of a more bioavailable final product, shows also the following advantages of technological nature:

1) The final product is purer since it is not contaminated by the salification agent.

2) The reaction time is very short (2-3 minutes) and warming the solution is not required.

3) Adding controlled amounts of acetone to the solution allows the avoidance of recrystallization of the product.

4) The solvent amounts involved are particularly reduced.

Magnesium alkoxides used according to the present invention are well-known and commercially available. Any of Magnesium ethoxide, propoxide or isopropoxide can be used.

The alcoholic solvent used will usually be chosen among the corresponding alcohols used as salificating agents. Methanol or ethanol will be preferred.

The product obtained according to the method of this invention has been compared with the magnesium valproate obtained as described in said ES patent N.430062 in pharmacokinetic tests in rats, after oral and intravenous administration. The new crystalline form obtained by the method above disclosed gives origin to higher and more prolonged hematic levels with respect to the reference magnesium salt. Hence the invention relates also to the pharmaceutical compositions containing magnesium valproate as a therapeutic agent, obtained according to the above method, prepared using conventional techniques and excipients, such as those described in Remington's Pharmaceutical Sciences Handbook, Mack. Publ. Co., N.Y. U.S.A.

Examples of pharmaceutical compositions include capsules, dragées, tablets, solutions, vials, syrups, suppositories and the like, containing from 0.1 to 1 g of therapeutic agent per unitary dose.

The following example further details the method of the invention.

EXAMPLE

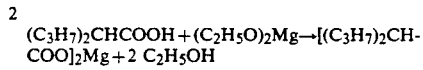

$$2(C_3H_7)_2CHCOOH + (C_2H_5O)_2Mg \rightarrow [(C_3H_7)_2CHCOO]_2Mg + 2 C_2H_5OH$$

A solution of 114 g of commercially available magnesium ethoxide and 300 ml of absolute ethanol is prepared, stirring for a short time.

To the so obtained magnesium ethoxide solution 288 g of di-isopropylacetic acid are added under stirring at room temperature. The salification is carried out in 2-3 minutes. 1000 ml of acetone are added to the obtained reaction mixture in 10 minutes. The reaction is stirred for further 5 minutes and then the resulting precipitate is filtered under vacuum. The isolated product is dried to constant weight. A colourless microcrystalline product is obtained with a 95% yield of the theoretic amount, with no further purifications.

| Elemental Analysis ($C_{16}H_{30}O_4Mg$; PM = 310.7): | | | |
|---|---|---|---|
| | C | H | Mg |
| Found | 62.1% | 9.9% | 7.7% |
| Calculated | 61.58% | 9.7% | 7.8% |

NMR Spectra ($D_2O$; 300 MHZ): 0.82-0.91 ppm (12H, t, $CH_3$); 1.2-1.5 ppm (16H, m, $CH_2$); 2.15-2.28 (2H, m, CHCO)

TLC: silica gel $F_{254}$ (Merck) 0.25 mm (toluene-methanol-acetone-$NH_4OH$ 25%:20/20/50/10) Rf: 0.5 (developer bromcresol green)

I claim:

1. A method of preparing magnesium valproate which comprises reacting valproic acid and a magnesium alkoxide selected from magnesium ethoxide, propoxide and isopropoxide in stoichiometric proportions in an alcoholic solvent selected from methanol and ethanol at room temperature and recovering magnesium valproate from the reaction mixture.

2. A method of preparing magnesium valproate which comprises reacting valproic acid and magnesium ethoxide in stoichiometric proporations in ethyl alcohol at room temperature and recovering magnesium valproate from the reaction mixture.

3. A method according to claim 2 in which acetone is added to the reaction mixture and crystalline magnesium valproate separated therefrom.

* * * * *